(12) United States Patent
Jones et al.

(10) Patent No.: US 7,983,734 B2
(45) Date of Patent: Jul. 19, 2011

(54) FIBROUS MARKER AND INTRACORPOREAL DELIVERY THEREOF

(75) Inventors: Michael L. Jones, San Clemente, CA (US); Paul Lubock, Laguna Niguel, CA (US); Lloyd H. Malchow, San Juan Capistrano, CA (US)

(73) Assignee: Senorx, Inc., Irvine, CA (US)

( * ) Notice: Subject to any disclaimer, the term of this patent is extended or adjusted under 35 U.S.C. 154(b) by 1362 days.

(21) Appl. No.: 10/444,770

(22) Filed: May 23, 2003

(65) Prior Publication Data
US 2004/0236212 A1 Nov. 25, 2004

(51) Int. Cl.
*A61B 6/00* (2006.01)

(52) U.S. Cl. .................. 600/431; 600/420; 600/426

(58) Field of Classification Search .................. 600/407, 600/414, 420, 426, 431, 437, 458, 424; 604/19; 606/116, 130
See application file for complete search history.

(56) References Cited

U.S. PATENT DOCUMENTS

| | | | |
|---|---|---|---|
| 2,192,270 A | 3/1940 | McGowan | |
| 3,341,417 A | 9/1967 | Sinaiko | |
| 3,818,894 A | 6/1974 | Wichterle et al. | |
| 3,823,212 A | 7/1974 | Chvapil | |
| 4,007,732 A | 2/1977 | Kvavle et al. | |
| 4,172,449 A | 10/1979 | LeRoy et al. | |
| 4,197,846 A | 4/1980 | Bucalo | |
| 4,276,885 A | 7/1981 | Tickner et al. | |
| 4,294,241 A | 10/1981 | Miyata | |
| 4,331,654 A | 5/1982 | Morris | |
| 4,390,018 A * | 6/1983 | Zukowski | 606/1 |
| 4,545,367 A | 10/1985 | Tucci | |
| 4,647,480 A | 3/1987 | Ahmed | |
| 4,693,237 A | 9/1987 | Hoffman et al. | |
| 4,813,062 A | 3/1989 | Gilpatrick | |
| 4,832,686 A | 5/1989 | Anderson | |
| 4,847,049 A | 7/1989 | Yamamoto | |
| 4,863,470 A | 9/1989 | Carter | |
| 4,909,250 A | 3/1990 | Smith | |
| 5,137,928 A | 8/1992 | Erbel et al. | |
| 5,147,307 A | 9/1992 | Gluck | |

(Continued)

FOREIGN PATENT DOCUMENTS

EP 0 146 699 9/1984

(Continued)

OTHER PUBLICATIONS

Collagen—Definitions from Dictionary.com.*

(Continued)

*Primary Examiner* — Tse Chen
*Assistant Examiner* — Peter Luong

(57) ABSTRACT

The invention is directed to an intracorporeal marker, a delivery device and assembly for such marker and the method of delivering one or more of the markers to an intracorporeal location within a patient. The marker is a body formed at least in part of a bioabsorbable fibrous material such as a fibrous mat or fabric. The delivery devices preferably also include one or more bioabsorbable short term markers which are configured to expand within the body cavity due to contacting a body fluid. The fibrous marker has a radiographically detectable member which preferably hold a portion of the fibrous body in a compressed condition. Preferably, the fibrous marker has a fibrous felt core formed of bioabsorbable material with a fabric jacket formed of bioabsorbable material. Therapeutic, diagnostic and binding agents may be incorporated into the fibrous body of the marker.

36 Claims, 3 Drawing Sheets

U.S. PATENT DOCUMENTS

| | | | |
|---|---|---|---|
| 5,221,269 A | 6/1993 | Miller et al. | |
| 5,236,410 A | 8/1993 | Granov et al. | |
| 5,281,408 A | 1/1994 | Unger | |
| 5,282,781 A | 2/1994 | Liprie | |
| 5,334,381 A | 8/1994 | Unger | |
| 5,368,030 A | 11/1994 | Zinreich et al. | |
| 5,394,875 A | 3/1995 | Lewis et al. | |
| 5,395,319 A | 3/1995 | Hirsh et al. | |
| 5,422,730 A | 6/1995 | Barlow et al. | |
| 5,433,204 A | 7/1995 | Olson | |
| 5,451,406 A | 9/1995 | Lawin et al. | |
| 5,469,847 A | 11/1995 | Zinreich et al. | |
| 5,494,030 A | 2/1996 | Swartz et al. | |
| 5,549,560 A | 8/1996 | Van de Wijdeven | |
| 5,580,568 A | 12/1996 | Greff et al. | |
| 5,629,008 A | 5/1997 | Lee | |
| 5,636,255 A | 6/1997 | Ellis | |
| 5,643,246 A | 7/1997 | Leeb et al. | |
| 5,646,146 A | 7/1997 | Faarup et al. | |
| 5,667,767 A | 9/1997 | Greff et al. | |
| 5,676,925 A | 10/1997 | Klaveness et al. | |
| 5,688,490 A | 11/1997 | Tournier et al. | |
| 5,695,480 A | 12/1997 | Evans et al. | |
| 5,782,775 A | 7/1998 | Milliman et al. | |
| 5,823,198 A | 10/1998 | Jones et al. | |
| 5,842,477 A | 12/1998 | Naughton et al. | |
| 5,851,508 A | 12/1998 | Greff et al. | |
| 5,853,366 A | 12/1998 | Dowlatshahi | |
| 5,902,310 A | 5/1999 | Foerster et al. | |
| 6,056,700 A | 5/2000 | Burney et al. | |
| 6,071,301 A | 6/2000 | Cragg et al. | |
| 6,161,034 A | 12/2000 | Burbank et al. | |
| 6,162,192 A | 12/2000 | Cragg et al. | |
| 6,181,960 B1 * | 1/2001 | Jensen et al. | 600/431 |
| 6,183,497 B1 | 2/2001 | Sing et al. | |
| 6,224,630 B1 | 5/2001 | Bao et al. | |
| 6,228,055 B1 | 5/2001 | Foerster et al. | |
| 6,234,177 B1 | 5/2001 | Barsch | |
| 6,251,418 B1 | 6/2001 | Ahern et al. | |
| 6,270,464 B1 | 8/2001 | Fulton, III et al. | |
| 6,316,522 B1 | 11/2001 | Loomis et al. | |
| 6,347,241 B2 | 2/2002 | Burbank et al. | |
| 6,350,244 B1 | 2/2002 | Fisher | |
| 6,356,782 B1 | 3/2002 | Sirimanne et al. | |
| 6,394,965 B1 | 5/2002 | Klein | |
| 6,450,937 B1 | 9/2002 | Mercereau et al. | |
| 6,540,981 B2 | 4/2003 | Klaveness et al. | |
| 6,544,185 B2 * | 4/2003 | Montegrande | 600/458 |
| 6,662,041 B2 * | 12/2003 | Burbank et al. | 600/431 |
| 6,725,083 B1 * | 4/2004 | Burbank et al. | 600/431 |
| 6,766,186 B1 | 7/2004 | Hoyns et al. | |
| 6,862,470 B2 | 3/2005 | Burbank et al. | |
| 2001/0003791 A1 | 6/2001 | Burbank et al. | |
| 2001/0006616 A1 | 7/2001 | Leavitt et al. | |
| 2001/0033867 A1 | 10/2001 | Ahern et al. | |
| 2001/0049481 A1 | 12/2001 | Fulton, III et al. | |
| 2002/0038087 A1 | 3/2002 | Burbank et al. | |
| 2002/0058882 A1 | 5/2002 | Fulton et al. | |
| 2002/0188196 A1 | 12/2002 | Burbank et al. | |
| 2003/0233101 A1 | 12/2003 | Lubock et al. | |
| 2004/0101479 A1 | 5/2004 | Burbank et al. | |
| 2004/0116806 A1 | 6/2004 | Burbank et al. | |
| 2004/0193044 A1 | 9/2004 | Burbank et al. | |
| 2004/0236211 A1 | 11/2004 | Burbank et al. | |
| 2004/0236213 A1 | 11/2004 | Jones et al. | |
| 2005/0045192 A1 | 3/2005 | Fulton et al. | |
| 2005/0063908 A1 | 3/2005 | Burbank et al. | |
| 2005/0065453 A1 | 3/2005 | Shabaz et al. | |
| 2005/0119562 A1 | 6/2005 | Jones et al. | |
| 2005/0143656 A1 | 6/2005 | Burbank et al. | |
| 2006/0036159 A1 | 2/2006 | Sirimanne et al. | |
| 2006/0036165 A1 | 2/2006 | Burbank et al. | |

FOREIGN PATENT DOCUMENTS

| | | |
|---|---|---|
| EP | 0 255 123 | 2/1988 |
| EP | 0 292 936 | 11/1988 |
| EP | 0 386 936 | 9/1990 |
| EP | 0 481 685 A1 | 10/1991 |
| EP | 0 458 745 A1 | 11/1991 |
| EP | 0 552 924 A | 7/1993 |
| EP | 1 493 451 | 1/2005 |
| GB | 708 148 | 4/1954 |
| WO | 91/12823 | 9/1991 |
| WO | 93/14712 | 5/1993 |
| WO | 93/17718 | 9/1993 |
| WO | 96/08208 A1 | 3/1996 |
| WO | 98/06346 | 2/1998 |
| WO | 99/30764 | 6/1999 |
| WO | WO 00/24332 | 5/2000 |
| WO | WO 00/38579 | 7/2000 |
| WO | WO 01/08578 A1 | 2/2001 |
| WO | WO 2004/105626 | 12/2004 |
| WO | WO 2005/039446 | 5/2005 |
| WO | WO 2005/089664 | 9/2005 |

OTHER PUBLICATIONS

Fibrous—Definitions from Dictionary.com.*

Armstrong, J. S., et al., "Differential marking of Excision Planes in Screened Breast lesions by Organically Coloured Gelatins", *Journal of Clinical Pathology*, Jul. 1990, No. 43 (7) pp. 604-607, XP000971447 abstract; tables 1,2.

Fucci, V., et al., "Large Bowel Transit Times Using Radioopaque Markers in Normal Cats", *J. of Am. Animal Hospital. Assn.*, Nov.-Dec. 1995 31 (6) 473-477.

Schindlbeck, N.E., et al., "Measurement of Colon Transit Time", *J. of Gastroenterology*, No. 28, pp. 399-404, 1990.

Shiga et al., Preparation of Poly(D, L-lactide) and Copoly(lactide-glycolide) Microspheres of Uniform Size, *J. Pharm. Pharmacol.* 1996 48:891-895.

* cited by examiner

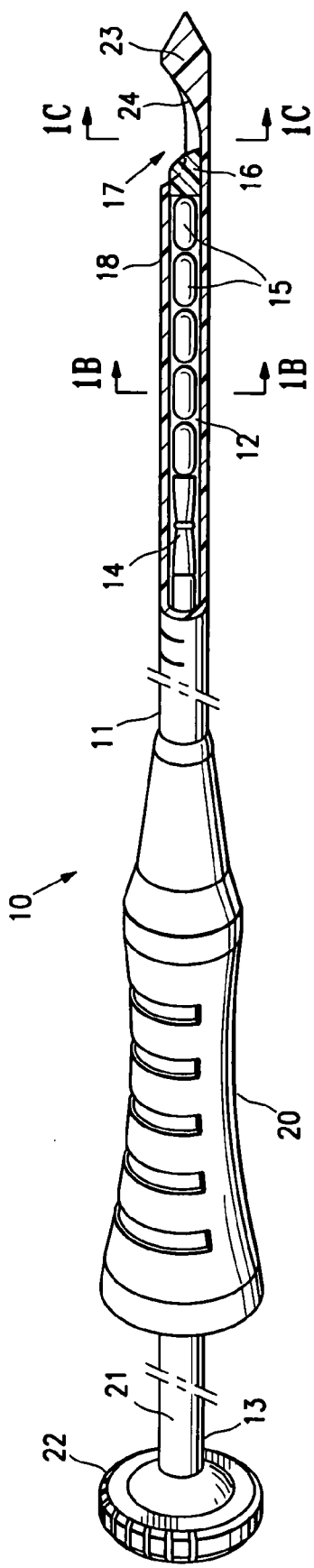
FIG. 1A
FIG. 1C
FIG. 1B

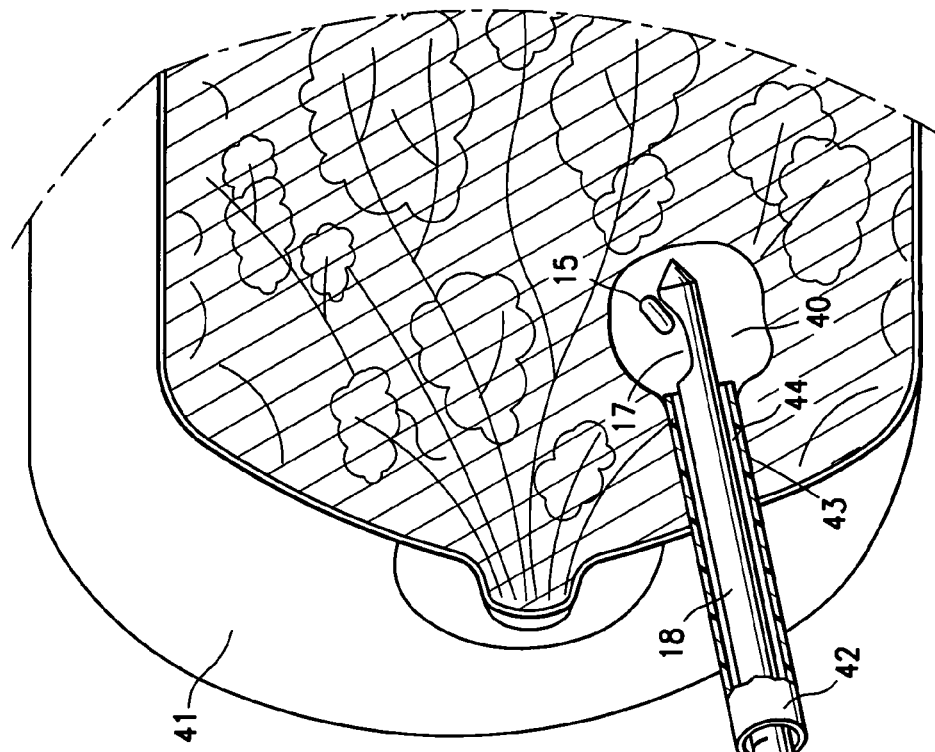
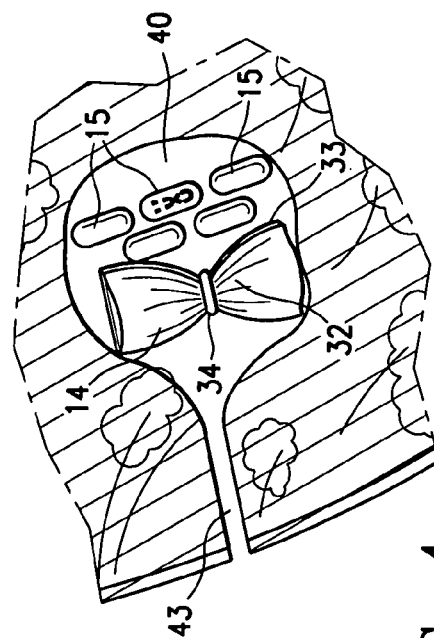
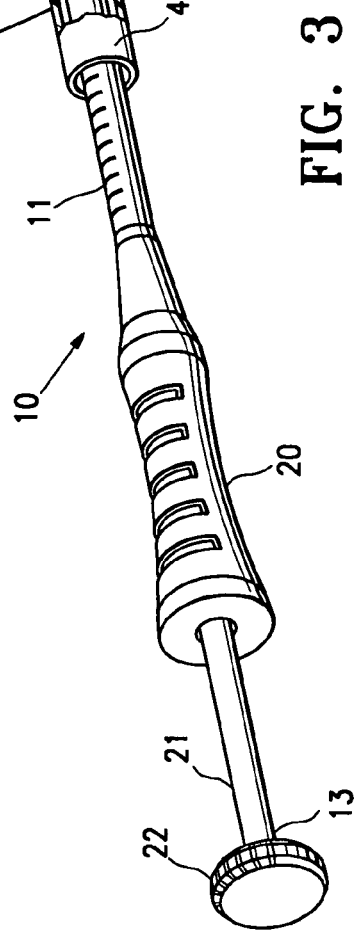
FIG. 3
FIG. 4

FIBROUS MARKER AND INTRACORPOREAL DELIVERY THEREOF

FIELD OF THE INVENTION

The invention is directed generally to a fibrous marker and devices and systems for the intracorporeal delivery thereof to a target site within a patient.

BACKGROUND OF THE INVENTION

In diagnosing and treating certain medical conditions, it is often desirable to mark a suspicious body site for the subsequent taking of a biopsy, delivery of medicine, radiation, or other treatment, to mark a location from which a biopsy was taken, or at which some other procedure was performed. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a therapeutic plan for the appropriate surgical procedure or other course of treatment.

In many instances, the suspicious tissue to be sampled is located in a subcutaneous site, such as inside a human breast. To minimize surgical intrusion into a patient's body, it is often desirable to insert a small instrument, such as a biopsy needle, into the body for extracting the biopsy specimen while imaging the procedure using fluoroscopy, ultrasonic imaging, x-rays, magnetic resonance imaging (MRI) or any other suitable form of imaging technique. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

Periodic physical examination of the breasts and mammography are important for early detection of potentially cancerous lesions. In mammography, the breast is compressed between two plates while specialized x-ray images are taken. If an abnormal mass in the breast is found by physical examination or mammography, ultrasound may be used to determine whether the mass is a solid tumor or a fluid-filled cyst. Solid masses are usually subjected to some type of tissue biopsy to determine if the mass is cancerous.

If a solid mass or lesion is large enough to be palpable, a tissue specimen can be removed from the mass by a variety of techniques, including but not limited to open surgical biopsy, a technique known as Fine Needle Aspiration Biopsy (FNAB) and instruments characterized as "vacuum assisted large core biopsy devices".

If a solid mass of the breast is small and non-palpable (e.g., the type typically discovered through mammography), a biopsy procedure known as stereotactic needle biopsy may be used. In performing a stereotactic needle biopsy of a breast, the patient lies on a special biopsy table with her breast compressed between the plates of a mammography apparatus and two separate x-rays or digital video views are taken from two different points of view. With the assistance of a clinician, a computer calculates the exact position of the lesion in the breast. Thereafter, a mechanical stereotactic apparatus is programmed with the coordinates and depth information calculated by the computer and such apparatus is used to precisely advance the biopsy needle into the lesion. Depending on the type of biopsy needle(s) used, this stereotactic technique may be used to obtain histologic specimens e.g., obtained through coring needle biopsy or, more commonly, a biopsy with a vacuum assisted large core biopsy device. Usually at least five separate biopsy specimens are obtained at or around the lesion.

The available treatment options for cancerous lesions of the breast include various degrees of lumpectomy or mastectomy and radiation therapy, as well as chemotherapy and combinations of these treatments. However, radiographically visible tissue features, originally observed in a mammogram, may be removed, altered or obscured by the biopsy procedure, and may heal or otherwise become altered following the biopsy. In order for the surgeon or radiation oncologist to direct surgical or radiation treatment to the precise location of the breast lesion several days or weeks after the biopsy procedure was performed, it is desirable that a biopsy site marker be placed in or on the patient's body to serve as a landmark for subsequent location of the lesion site. A biopsy site marker may be a permanent marker (e.g., a metal marker visible under X-ray examination), or a temporary marker (e.g., a bioresorbable marker detectable with ultrasound). While current radiographic type markers may persist at the biopsy site, an additional mammography generally must be performed at the time of follow up treatment or surgery in order to locate the site of the previous surgery or biopsy. In addition, once the site of the previous procedure is located using mammography, the site must usually be marked with a location wire which has a hook on the end which is advanced into site of the previous procedure. The hook is meant to fix the tip of the location wire with respect to the site of the previous procedure so that the patient can then be removed from the confinement of the mammography apparatus and the follow-up procedure performed. However, as the patient is removed from the mammography apparatus, or otherwise transported the position of the location wire can change or shift in relation to the site of the previous procedure. This, in turn, can result in follow-up treatments being misdirected to an undesired portion of the patient's tissue.

As an alternative or adjunct to radiographic imaging, ultrasonic imaging and visualization techniques (herein abbreviated as "USI") can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. Such a marker enables a follow-up procedure to be performed without the need for traditional radiographic mammography imaging which, as discussed above, can be subject to inaccuracies as a result of shifting of the location wire as well as being tedious and uncomfortable for the patient.

Placement of a marker or multiple markers at a location within a patient's body requires delivery devices capable of holding markers within the device until the device is properly situated within a breast or other body location. Accordingly, devices and methods for retaining markers within a marker delivery device while allowing their expulsion from the devices at desired intracorporeal locations are desired.

SUMMARY OF THE INVENTION

The invention is directed to a fibrous, swellable marker which positions a long-term radiographically detectable marker element within a target site of a patient's body. Preferably, short term ultrasound detectable markers are also delivered into the target site along with the fibrous marker.

The fibrous marker embodying features of the invention is formed at least in part of a fibrous material, such as oxidized, regenerated cellulose, polylactic acid, a copolymer of polylactic acid and glycolic acid, polycaprolactone, in a felt and/or fabric or woven structure. The fibrous marker material is swellable in the presence of body fluid, such as blood or plasma, or other water based fluid. The fibrous material is formed into an elongated member and bound in a compressed condition to provide sufficient column strength to facilitate introduction into and discharge from a tubular delivery device. Suitable binding agents for holding the fibrous marker in a compressed condition are water soluble polymers such as polyvinyl alcohol, polyethylene glycol, polyvinyl pyrollidone. One or more radiographically detectable marker elements are provided with the fibrous marker, preferably centrally located, to ensure that the radiographically detectable element is disposed at a more or less central location within the target site rather than at a site margin.

The one or more short term ultrasonically detectable markers, which are preferably delivered with the fibrous markers, are formed of bioabsorbable materials. Details of suitable short term ultrasonically detectable markers can be found in U.S. Pat. No. 6,161,034, issued Dec. 12, 2000, U.S. Pat. No. 6,347,241, issued Feb. 12, 2002, application Ser. No. 09/717,909, filed Nov. 20, 2000, now U.S. Pat. No. 6,725,083, and application Ser. No. 10/124,757, filed Apr. 16, 2002, now U.S. Pat. No. 6,862,470. These patents and applications are assigned to the present assignee and are incorporated herein in their entirety by reference.

Marker delivery systems embodying features of the invention include an elongated cannula with an inner lumen extending therein and a discharge opening or port in a distal portion of the cannula which is in fluid communication with the inner lumen. The fibrous marker embodying features of the invention is slidably disposed within the inner lumen of the cannula, preferably along with at least one short term marker. The short term marker is preferably disposed distal to the fibrous marker so that upon discharge from the cannula into a target site cavity, the fibrous marker will swell upon contact with body fluids to block the accessing passageway. The discharge opening of the delivery device is preferably closed with a plug to hold in the markers during handling and delivery and to prevent tissue and fluid from entering the inner lumen through the discharge opening during delivery. Any water based fluid which may enter into the inner lumen of the delivery device can result in the expansion or swelling of the marker bodies within the inner lumen and prevent their deployment. Preferably, the plug is formed of a water swellable material, so that the plug occludes the opening upon contact with a water based fluid and thereby prevents the premature expansion of the markers within the inner lumen. The plug is easily pushed out of the discharge opening of the tubular delivery device.

A movable plunger is slidably disposed within the inner lumen of the delivery cannula from an initial position accommodating the marker or markers and the plug within the tube, to a delivery position to push a marker against the plug to push the plug out of the discharge opening and to then eject one or more markers through the opening into the target tissue site.

Upon being discharged into the intracorporeal target site, the fibrous marker swells on contact with body fluid, e.g. blood. The expanded fibrous marker fills or partially fills the cavity at the target site, positioning the radiopaque marker element within the interior of the target cavity. Additionally, a therapeutic agent, a diagnostic agent or other bioactive agent may be incorporated into the fibrous marker body. Such agents include a hemostatic agent to accelerate thrombus formation within the target cavity, an anesthetic agent, a coloring agent, an antibiotic agent, an antifungal agent, an antiviral agent, a chemotherapeutic agent, a radioactive agent and the like.

The plug secures the discharge opening on the distal portion of the cannula, but it is easily ejected or removed from the orifice, allowing the delivery of the markers to a desired site within a patient's body. The plug or the cannula itself may have retaining features, such as recesses, protuberances, detents and the like which are configured to releasably retain the plug or the short term markers proximal to the plug until ejection of the plug from the delivery tube is desired. The retaining features may be complementary pairs, such as a plug protuberance configured to fit into a recess in the cannula interior. For further plug details see co-pending application Ser. No. 10/174,401, filed on Jun. 17, 2002, entitled Plugged Tip Delivery Tube For Marker Placement. This application is assigned to the present assignee and is incorporated herein in its entirety by reference.

The invention provides the advantages of a relatively long term fibrous marker which is easily deployed into a target site and which positions a permanent radiographically detectable marker element within a central portion of the target site. When combined with short term ultrasound markers, the target site is easily detected at a later date by personnel with minimal training. These and other advantages of the invention will become more apparent from the following description when taken in conjunction with the accompanying drawings.

BRIEF DESCRIPTION OF THE DRAWINGS

FIG. 1A is a partly cut-away perspective view of a marker delivery assembly showing a fibrous marker embodying features of the invention and several short term markers within a marker delivery device and a plug embodying occluding the discharge opening of the delivery device.

FIG. 1B is a transverse cross-sectional view of the marker delivery assembly of FIG. 1A taken at line 1B-1B.

FIG. 1C is a transverse cross-sectional view of the marker delivery assembly of FIG. 1A taken at line 1C-1C.

FIG. 3 is a partially cut away, perspective view of a human breast having a biopsy cavity from which a biopsy specimen has been removed, and showing the delivery of a marker to the cavity.

FIG. 4 schematically illustrates the deployment of a plurality of markers, including a marker embodying features of the invention, into a biopsy cavity.

DETAILED DESCRIPTION OF THE INVENTION

Figure 2C:
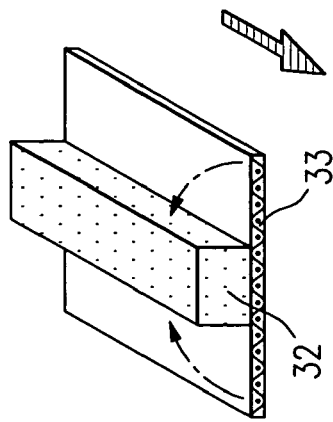
FIGS. 2A-2F schematically illustrate the manufacture and use of a fibrous marker embodying features of the invention.
Figure 2B:
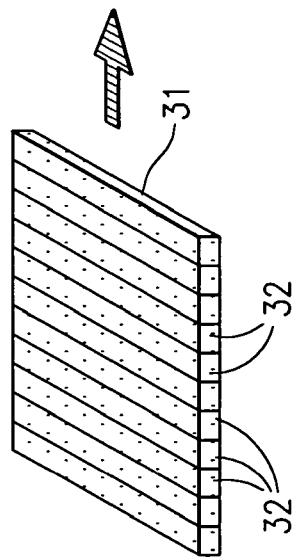
Figure 2A:
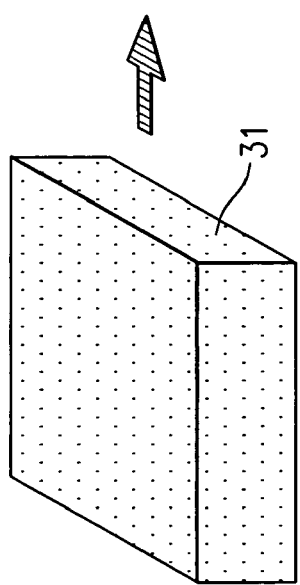
Figure 2D:
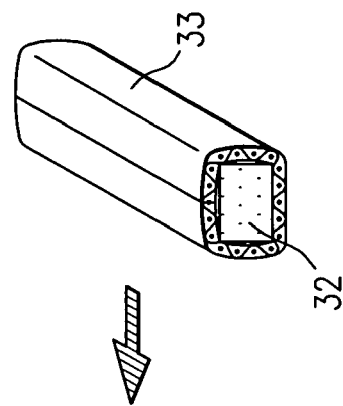
Figure 2E:
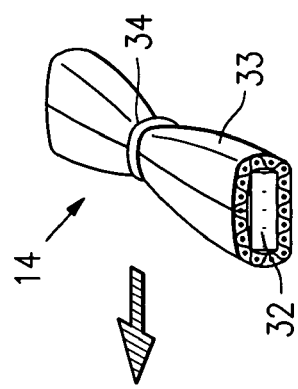

A marker delivery assembly 10 embodying features of the invention and illustrated in FIGS. 1A-1C, includes a marker delivery cannula 11 which has an inner lumen 12, a plunger 13 slidably disposed within the inner lumen 12, a fibrous marker 14 and a plurality of short term ultrasonically detectable markers 15 slidably disposed within the inner lumen, and a plug 16 occluding a discharge opening 17 in the distal portion of the cannula 11. The delivery cannula 11 has an elongated shaft 18 which defines at least in part the inner lumen 12 and has a handle 20 on the proximal end of the cannula shaft 18 to facilitate handling and advancement of the device. The plunger 13 has a plunger shaft 21 and a plunger handle 22 to facilitate advancement of the plunger shaft 21 within inner lumen 12 of cannula 11 to discharge markers 14 and 15 from the discharge opening 17 in the cannula. As shown a plurality of short term ultrasonically detectable markers 15 are disposed within the inner lumen 12 distal to the fibrous marker 14. The cannula 11 has a sharp, tissue penetrating distal tip 23 to facilitate advancement through tissue to the target site within the patient. A ramp 24 within the discharge opening 17 of the cannula 11 is provided to guide the markers 14 and 15 out through the discharge opening 17.

The manufacture and use of fibrous marker 14 is schematically illustrated in FIGS. 2A-2F. A felt pad or mat 31 of oxidized, regenerated cellulose about 0.125 to about 0.375 inch (3.2-9.3 mm), preferably about 0.25 inch (6.4 mm) thick is compressed and impregnated with a 10% (Wt.) polyethylene glycol in a 70% isopropyl alcohol solution to a mat about 0.03 to about 0.05 inch (0.76-1.3 mm) thick with a length of about 20 mm. A reduction in thickness of 80% or more may be suitable. The compressed mat 31 is cut up into elongated strips 32 with square or near square transverse cross-sectional shapes. The strips 32 are wrapped in a fabric 33 of oxidized regenerated cellulose about 5 to about 10 mm in width and about 20 mm in length, compressed and impregnated with a 10% PEG dispersion and then dried at elevated temperatures (e.g. about 70° F. to about 150° F.) to a diameter of about 0.065 inch (1.65 mm). The fabric 33 should make at least one, preferably two or more complete wraps about the strip 32. The wrapped and compressed strip may then be cut to a desired length to form the fibrous marker 13. Alternatively, the uncompressed mat 31, the strip 32 and fiber wrap 33 may be provided at the desired length for the fibrous marker 13. A radiographically detectable marker element 34 may be formed of a radiopaque material such as 316L stainless steel or titanium wire 35 (OD about 0.005-0.01 inch, 0.13-0.25 mm) may then be crimped about or embedded in a central portion (or other desired portion) of the marker 14. The fibrous marker 14 is then ready for deployment.

The delivery of the markers into the target site within a human patient is illustrated in FIG. 3. In this particular illustration, the biopsy specimen has already been removed leaving a cavity 40 with the patient's breast 41. A guide cannula 42 remains in the patient from the biopsy procedure. Marker delivery assembly 10 is held by the handle 20 and the shaft 18 thereof containing the markers 14 and 15 is introduced into the inner lumen 44 of the guide cannula 42. The delivery cannula 11 is advanced within the inner lumen 44 until the discharge opening 17 of the delivery cannula is disposed within the cavity 40. The operator then presses the handle 22 on plunger 13 to eject markers 14 and 15 out the discharge opening 17. The pressure on the markers 14 and 15 is sufficient to dislodge the plug 16 which closes off the discharge opening 17. A ramp 24 provided in the discharge opening 17 ensures that the markers 14 and 15 and plug 16 are discharged from the delivery device into the biopsy cavity 40.

Figure 2F:
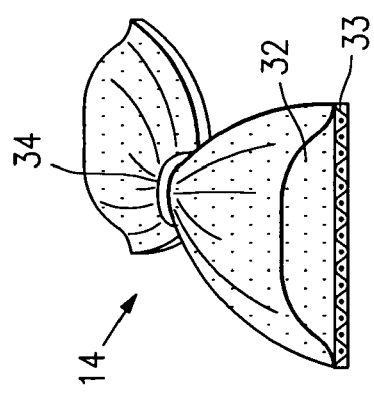

Once the markers 14 and 15 are disposed within the biopsy cavity 40, the fibrous marker 14 begins to swell from the body fluids located in the biopsy cavity. The short term, markers 15 are preferably ejected first and the fibrous marker 14 ejected last. This allows the fibrous marker 14 to swell and unfurl so as to extend across a significant portion of the cavity 40. With a radiographically detectable wire or clip holding a central portion of the marker 14 in a constricted condition, the marker expands into a bow-tie could also place clip/wire to allow full unrolling form rectangular mat shape, as shown in FIG. 4, to center the radiopaque marker element 34 within the cavity 40. This expansion will also tend to block off the accessing passageway 43 leading to the cavity 40 to prevent excursions of the markers 14 or other elements back into the passageway 43 which can cause the physician to miss the biopsy site cavity on subsequent examination. The marker 14 is schematically illustrated in FIG. 2F as having felt layer 32 over the entire surface of fabric layer 33. However, in a clinical setting the layer 32 will cover only a portion of the layer 33.

The fibrous marker is preferably formed of a felt and/or fiber material formed of oxidized regenerated cellulose. However, the fibrous marker may be formed of a bioabsorbable polymer such as polylactic acid, a co-polymer of polylactic acid and glycolic acid, polycaprolactone, collagen and mixtures thereof, including mixtures with oxidized regenerated cellulose. Suitable oxidized, regenerated cellulose includes SURGICEL™ from the Ethicon Division of Johnson & Johnson or other suitably oxidized regenerated cellulose. The fibrous marker may be formed of naturally hemostatic materials such as oxidized, regenerated cellulose or a hemostatic agent such as collagen or gelatin may be incorporated into the fibrous material to provide the hemostasis upon contact with blood. A wide variety of other hemostatic agents may be incorporated into the marker. The thrombus formed by the hemostasis is formed very quickly to fill the cavity at the biopsy site and at least temporarily hold the markers 14 and 15 in position within the cavity. Anesthetic agents to control post procedure pain, chemotherapeutic agents to kill any residual neoplastic tissue, coloring agents (e.g. carbon black and methylene blue) for visual location of the biopsy site, may also be incorporated into the fibrous marker.

The radiopaque marker element is preferably clamped about the exterior of the fibrous material. However, a suitable radiopaque marker may be incorporated or otherwise embedded into the fibrous material to facilitate the location of the marker element by the fibrous marker within the biopsy cavity. The fibrous marker is generally configured to be slidably disposed within the inner lumen of the delivery cannula, and before delivery is about 0.5 mm to about 12 mm, preferably about 1 to about 8 mm in diameter and about 5 to about 30 mm, preferably about 10 to about 25 mm in length. Upon contact with a body fluid or other water based fluid, the length of the fibrous marker remains about the same but the wrapped structure unfolds upon swelling to a width of about 5 to about 25 mm, usually about 10 to about 20 mm. With a radiopaque marker element clamped about a center portion of the wrapped fibrous marker, the fibrous marker expands into a generally bow-tie shape when exposed to body fluids. However, even though secured to the fibrous marker, the radiopaque marker element need not restrict the expansion of the fibrous marker.

The short term marker, which is primarily designed for ultrasound detection over a period of several hours to several months, is preferably formed of a bioabsorbable material such as polylactic acid-glycolic acid copolymer. However, the short term marker may be formed of other bioabsorbable materials including polylactic acid and porcine gelatin. The short term marker materials are processed to include bubbles about 20 to about 1000 micrometers in diameter for ultrasound detection. The bubble formation is preferably formed by the addition of sodium bicarbonate, but air may be physically incorporated while mixing the bioabsorbable material. The life of a particular short term marker may be controlled by the molecular weight of the polymer material from which it is made, with the higher molecular weights providing longer marker life. Suitable short term markers include the GelMark, which is a gelatin based marker, and GelMark Ultra which is a polylactic acid-glycolic acid copolymer based marker, sold by the present assignee. See also U.S. Pat. Nos. 6,161,034, 6,427,081, 6,347,241 and co-pending application Ser. No. 09/717,909, filed on Nov. 20, 2000 and co-pending application Ser. No. 10/174,401, filed on Jun. 17, 2002 which are incorporated herein by reference in their entirety. The short term markers are configured to be slidably disposed within the inner lumen of the delivery cannula and generally are about 0.5 mm to about 12 mm, preferably about 1 to about 3 mm in diameter, typically about 1.5 mm, and about 1 to about 20 mm, preferably about 2.5 to about 15 mm in length. The short term markers are preferably shorter than the fibrous marker.

The plug used to occlude the discharge opening of the delivery cannula may be formed of the same material as the short term marker and indeed may be employed as a short term marker itself. The plug is preferably formed of or coated with polyethylene glycol which readily hydrates in the presence of body fluids and which causes the plug to swell and occlude the discharge opening. This prevents premature contact between body fluids and the markers within the inner lumen of the delivery device which can cause the markers to swell in the lumen and prevent or retard their deployment to the target site.

An operator may grasp a device handle 20 to guide the device 10 during insertion, and to steady the device 10 during depression of the plunger 13. Insertion of a device 10 results in the placement of at least a portion of the device 10 adjacent a desired location. The device 10, in particular the distal tip 23 and orifice 17 of the device 10, may be guided adjacent a desired location such as a lesion site, or a biopsy cavity, or other internal body site where delivery of a marker 14 is desired.

The short term marker typically should remain in place and be detectable within a patient for a period of at least 2 weeks to have practical clinical value, preferably at least about 6 weeks, and may remain detectable for a time period of up to about 20 weeks, more preferably for a time period of up to about 12 weeks. The fibrous marker should have a life period of short duration, e.g. less than 30 days but the radiographically detectable marker element of the fibrous marker should have a life of at least one year and preferably is permanently radiographically detectable While stainless steel and titanium are preferred radiopaque materials, the radiopaque elements may be made of suitable radiopaque materials such as platinum, gold, iridium, tantalum, tungsten, silver, rhodium, nickel, NiTi alloy. MRI contrast agents such as gadolinium and gadolinium compounds, for example, are also suitable for use with plugs and/or markers embodying features of the invention.

Marker delivery devices other than those shown in FIGS. 1A-1C may be employed. Other suitable delivery devices are depicted in U.S. Pat. No. 6,347,241 and co-pending application Ser. No. 09/717,909 which have been incorporated herein by reference.

While particular forms of the invention have been illustrated and described herein, it will be apparent that various modifications and improvements can be made to the invention. Moreover, those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action.

All patents and patent applications referred to above are hereby incorporated by reference in their entirety.

What is claimed is:

1. An intracorporeal marker comprising a pushable fibrous unitary marker body comprising bioabsorbable fibers compressed into a desired compressed configuration, and bound in the desired compressed configuration by a polymer binding agent, and which has a radiopaque marker element.

2. The intracorporeal marker of claim 1 wherein the radiopaque marker element is incorporated into the marker body.

3. The intracorporeal marker of claim 1 wherein the radiopaque marker element is disposed about the marker body.

4. The intracorporeal marker of claim 3 wherein the radiographically detectable marker element is a radiopaque wire element clamped about a central exterior portion of the marker body.

5. The intracorporeal marker of claim 1 wherein the bioabsorbable fibers of the marker body comprise a bioabsorbable material selected from the group consisting of cellulose, polylactic acid, a copolymer of polylactic acid and glycolic acid, and polycaprolactone.

6. The intracorporeal marker of claim 5 wherein the cellulose is oxidized, regenerated cellulose.

7. The intracorporeal marker of claim 1 wherein the fibers of the marker body swell in the presence of body fluids or other water based fluids.

8. The intracorporeal marker of claim 1 wherein the bioabsorbable fibers have been woven into fabric.

9. The intracorporeal marker of claim 1 wherein the bioabsorbable fibers comprise felt fabric.

10. The intracorporeal marker of claim 1 wherein the marker body is ultrasonically detectable.

11. The intracorporeal marker of claim 1 wherein the marker body includes at least one bioactive component selected from the group consisting of therapeutic and diagnostic agents incorporated therein.

12. The intracorporeal marker of claim 11 wherein the incorporated therapeutic or diagnostic agent is selected from the group consisting of a hemostatic agent, an anesthetic agent, a coloring agent, an antibiotic agent, an antifungal agent, an antiviral agent, a chemotherapeutic agent and a radioactive agent.

13. The intracorporeal marker of claim 1 wherein the bioabsorbable fibers comprise a material selected from the group consisting of polylactic acid, a co-polymer of polylactic acid and glycolic acid, polycaprolactone, collagen and mixtures thereof, including mixtures with oxidized cellulose.

14. The intracorporeal marker of claim 1 wherein the radiographically detectable marker element is disposed at a central portion of the marker body.

15. The intracorporeal marker of claim 1 wherein a constricting member holds a portion of the marker body to prevent its expansion upon contact with a water based fluid.

16. The intracorporeal marker of claim 15 wherein the constricting member holds a central portion of the marker body to prevent its expansion.

17. The intracorporeal marker of claim 1 wherein the radiographically detectable marker element is a constricting member which holds a portion of the marker body to prevent its expansion.

18. The intracorporeal marker of claim 17 wherein the radiographically detectable constricting member holds a central portion of the marker body to prevent its expansion.

19. The intracorporeal marker of claim 18 wherein the constricted marker body is configured to expand into a bowtie shape when exposed to body fluid or other water based fluid.

20. The intracorporeal marker of claim 1 wherein the marker body has been compressed at least 25%.

21. An intracorporeal marker delivery device for a tissue site, comprising:
  an elongated delivery cannula which has a distal tip, an inner lumen and a discharge opening in communication with the inner lumen;
  at least one short term ultrasonically detectable marker body which is slidably disposed within the inner lumen of the delivery cannula proximal to the discharge opening; and
  at least one fibrous unitary marker body comprising bioabsorbable fibers which is compressed into a desired configuration and bound in the desired compressed configuration by a binding agent prior to insertion into the inner lumen of the delivery cannula, which has a radiographic imageable element, which is slidably disposed within and pushable through the inner lumen of the delivery cannula proximal to the discharge opening and which is configured to position the radiographic detectable element within a cavity at a tissue site.

22. The intracorporeal marker delivery device of claim 21 wherein the fibers of the at least one marker body are expandable upon contact with body fluid or other water based fluid.

23. The intracorporeal marker delivery device of claim 21 wherein the discharge opening of the delivery cannula is occluded by a bioabsorbable plug to prevent the premature contact of the at least one fibrous marker body within the inner lumen with body fluids at the tissue site.

24. The intracorporeal marker delivery device of claim 21, wherein the discharge opening of the delivery cannula is occluded by a bioabsorbable plug, and the bioabsorbable plug is comprised of material which expands upon contact with body fluid to occlude the discharge opening of the delivery cannula to prevent the premature contact of the at least one fibrous marker body within the inner lumen with the body fluid at the tissue site.

25. The intracorporeal marker delivery device of claim 21 wherein the radiographically detectable element surrounds an exterior portion of the at least one marker body bioabsorbable fibers.

26. The intracorporeal marker delivery device of claim 21 wherein the at least one marker body is disposed within the inner lumen of the cannula proximal to the short term marker.

27. The intracorporeal marker of claim 21 wherein the binding agent comprises one or more of water soluble polymers selected from the group consisting of polyvinyl alcohol, polyethylene glycol, polyvinyl pyrollidone.

28. An intracorporeal marker delivery system, comprising:
  an intracorporeal marker delivery device including an intracorporeal delivery cannula which has a tissue penetrating distal tip, an inner lumen and a discharge opening in communication with the inner lumen; and
  at least one marker disposed within the inner lumen of the delivery cannula, each marker having an expandable and pushable unitary marker body comprising bioabsorbable fibers comprising a compressed felt, fabric or woven structure with at least one radiographically detectable marker element, the compressed felt, fabric or woven structure being compressed into a desired compressed configuration and bound in the desired compressed configuration by a polymer binding agent.

29. A method of marking a desired intracorporeal location within a patient, comprising:
  a. providing a delivery cannula having an inner lumen and a discharge opening in a distal portion thereof;
  b. providing at least one marker which includes an expandable fibrous unitary marker body comprising bioabsorbable fibers having a felt, fabric or woven structure, which has been compressed into a compressed configuration and bound in the compressed configuration with a polymer binding agent before being inserted into the inner lumen of the delivery cannula, which has at least one radiographically detectable marker element and which is slidably disposed within the inner lumen of the delivery cannula;
  c. inserting the delivery cannula with the at least one marker body into a patient;
  d. advancing the delivery cannula within the patient until the distal portion of the cannula is disposed within a desired intracorporeal location; and
  e. pushing the at least one marker body through the inner lumen of the cannula and discharging the at least one marker body from an opening in a distal portion of the cannula into the desired intracorporeal location.

30. An intracorporeal marker delivery device for a tissue site, comprising:
  an elongated tubular delivery means which has a distal tip, an inner lumen and a discharge opening in communication with the inner lumen;
  at least one short term ultrasonically detectable marker means which is slidably disposed within the inner lumen of the delivery means; and
  at least one pushable unitary marker comprising bioabsorbable strands in a felt, fabric or woven structure, compressed to a compressed configuration and bound in the compressed configuration by a polymer binding agent prior to insertion into the inner lumen of the delivery cannula, which has a radiographic imageable element, which is slidably disposed within the inner lumen of the delivery means and which is configured to position the radiographic detectable element within a cavity at a tissue site.

31. A method of marking a desired intracorporeal location within a patient, comprising:
  a. providing a delivery cannula having a distal tip, an inner lumen and a discharge opening in a distal portion thereof;
  b. providing at least one marker which includes an expandable bioabsorbable fibrous unitary marker body comprising bioabsorbable fibers in a felt, fabric or woven structure, compressed to a compressed configuration and bound in the compressed configuration by a polymer binding agent prior to insertion into the inner lumen of the delivery cannula, which has at least one radiographically detectable marker element and which is slidably disposed within the inner lumen of the delivery cannula;
  c. a step of inserting the distal portion of the delivery cannula into a patient;
  d. a step of advancing the delivery cannula within the patient until the distal portion of the cannula is disposed within a desired intracorporeal location; and e. a step of pushing the at least one marker through the inner lumen of the cannula and discharging the at least one marker from the discharge opening in the distal portion of the cannula into the desired intracorporeal location.

32. An intracorporeal marker delivery device for a tissue site, comprising:
 a) an elongated delivery cannula which has a distal tip, an inner lumen and a discharge opening in communication with the inner lumen;
 b) at least one remotely detectable unitary marker body comprising bioabsorbable fibers in a felt, fabric or woven structure, compressed into a compressed configuration and bound in the compressed configuration by a polymer binding agent prior to insertion into the inner lumen of the delivery cannula, and which is slidably disposed within and pushable through the inner lumen of the delivery cannula; and
 c) a distal tip plug which expands in the presence of body fluids, which is disposed at least in part within a distal portion of the inner lumen distal to the remotely detectable marker body and which partially occludes the discharge opening in the delivery cannula.

33. The intracorporeal marker delivery device of claim 32 wherein the distal tip plug comprises at least in part polyethylene glycol.

34. The intracorporeal marker delivery device of claim 32 wherein the marker body is expandable upon contact with body fluid or other water based fluid.

35. The intracorporeal marker delivery device of claim 32 wherein a radiographically detectable element surrounds an exterior portion of the marker body.

36. The intracorporeal marker delivery device of claim 32 including a plunger which is slidably disposed within the inner lumen of the cannula and which has a distal end proximal to marker bodies in the inner lumen.

\* \* \* \* \*